US012611171B2

(12) United States Patent
Nikolov et al.

(10) Patent No.: US 12,611,171 B2
(45) Date of Patent: Apr. 28, 2026

(54) SYSTEM, METHOD AND/OR COMPUTER READABLE MEDIUM FOR ADAPTIVE SPATIAL COMPOUNDING IN ULTRASOUND BASED ON PROBABILITIES DETERMINED FROM AN ESTIMATED SNR

(71) Applicant: GE Precision Healthcare LLC, Waukesha, WI (US)

(72) Inventors: Svetoslav Ivanov Nikolov, Søborg (DK); Amalie Sofie Ekstrand, København (DK); Matthias Bo Stuart, Hørsholm (DK)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 29 days.

(21) Appl. No.: 18/614,401

(22) Filed: Mar. 22, 2024

(65) Prior Publication Data

US 2025/0295380 A1 Sep. 25, 2025

(51) Int. Cl.
| | |
|---|---|
| *A61B 8/14* | (2006.01) |
| *A61B 8/00* | (2006.01) |
| *A61B 8/08* | (2006.01) |

(52) U.S. Cl.
CPC .............. *A61B 8/145* (2013.01); *A61B 8/085* (2013.01); *A61B 8/4488* (2013.01);
(Continued)

(58) Field of Classification Search
CPC .. A61B 8/4488; A61B 8/5253; G01S 15/8995
See application file for complete search history.

(56) References Cited

U.S. PATENT DOCUMENTS 5,582,173 A * 12/1996 Li ....................... G01S 15/8993
600/443
6,423,004 B1 7/2002 Dong et al.
(Continued)

FOREIGN PATENT DOCUMENTS

CN 112263274 A 1/2023

OTHER PUBLICATIONS

Jespersen, et al., Multi-Angle Compound Imaging, Ultrasonic Imaging, Apr. 1998, sheets 11, https://journals.sagepub.com/doi/pdf/10.1177/016173469802000201?download=true, Abstract.
(Continued)

*Primary Examiner* — Nyrobi Celestine
(74) *Attorney, Agent, or Firm* — Daugherty & Del Zoppo, Co. LPA

(57) ABSTRACT

An ultrasound imaging system includes a transducer array configured to transmit a plurality of ultrasound signals, each at a different angle of insonation, receive, for each of the plurality of ultrasound signal, an echo signal, and generate an electrical signal indicative of each of the echo signals. A beamformer is configured to beamform the electrical signals and produce a radio frequency (RF) signal for each of the different angles of insonation. An envelope detector is configured to detect an envelope of each of the RF signals for each of the different angles of insonation. A compressor is configured to compress each of the envelopes to produce frames of data for each of the different angles of insonation. A compounder is configured to adaptively compound the frames of data for each of the different angles of insonation to generate a compounded image. A display is configured to display the compounded image.

20 Claims, 8 Drawing Sheets

(52) U.S. Cl.
     CPC ............ *A61B 8/4494* (2013.01); *A61B 8/461*
                 (2013.01); *A61B 8/5207* (2013.01); *A61B*
                                         *8/5253* (2013.01)

(56)                    References Cited

U.S. PATENT DOCUMENTS

| | | | |
|---|---|---|---|
| 6,508,770 | B1 | 1/2003 | Cai |
| 6,547,732 | B2 | 4/2003 | Jago |
| 8,956,300 | B2 | 2/2015 | Guo et al. |
| 11,087,466 | B2 | 8/2021 | Vignon et al. |
| 2006/0078181 | A1* | 4/2006 | Chen .......................... G06T 5/50 |
| | | | 382/128 |
| 2012/0157850 | A1 | 6/2012 | Sumi et al. |
| 2016/0296203 | A1* | 10/2016 | Konofagou .............. A61B 8/14 |
| 2017/0301094 | A1 | 10/2017 | Vignon et al. |
| 2020/0202518 | A1* | 6/2020 | Vignon ................ A61B 8/4245 |

OTHER PUBLICATIONS

Hasegawa, Converting Coherence to Signal-to-noise Ratio for Enhancement of Adaptive Ultrasound Imaging, Ultrasonic Imaging, Jan. 2020, pp. 27-40 (25 sheets), vol. 42, issue 1, HTTP://doi.org/10.1177/0161734619889384.

* cited by examiner

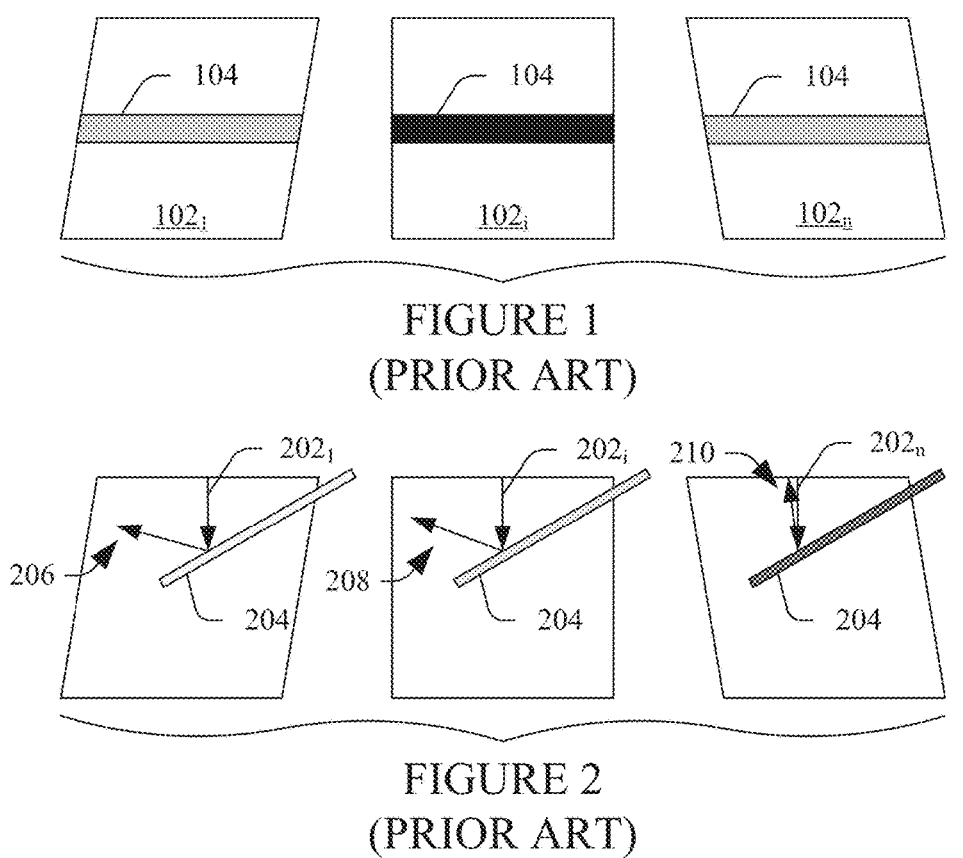
FIGURE 1
(PRIOR ART)
FIGURE 2
(PRIOR ART)
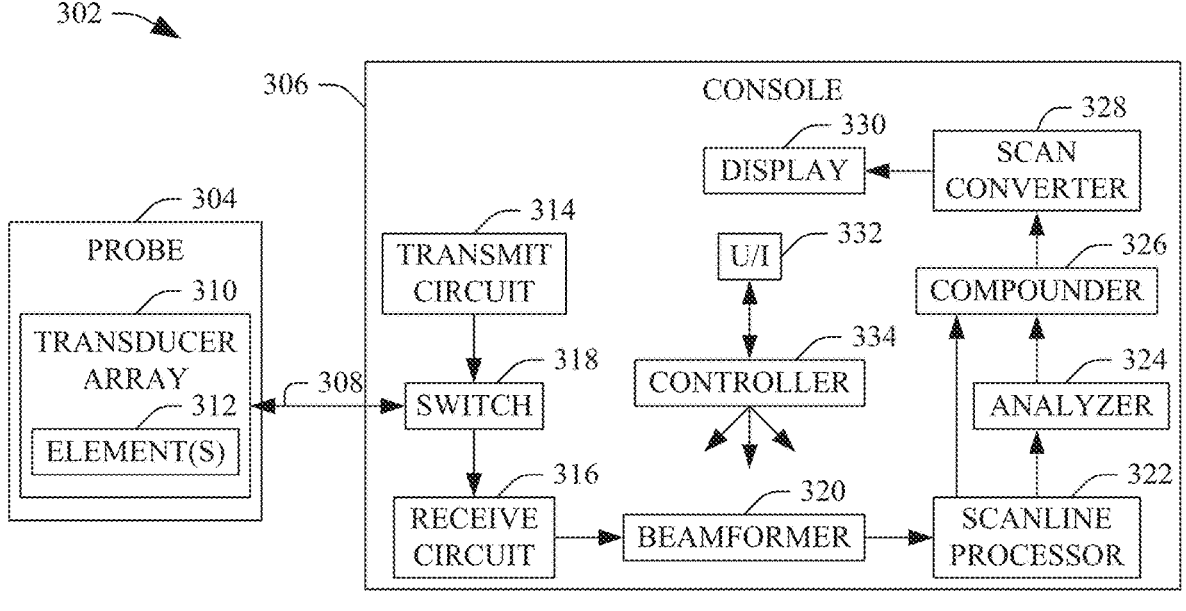
FIGURE 3

SYSTEM, METHOD AND/OR COMPUTER READABLE MEDIUM FOR ADAPTIVE SPATIAL COMPOUNDING IN ULTRASOUND BASED ON PROBABILITIES DETERMINED FROM AN ESTIMATED SNR

FIELD

The following generally relates to ultrasound, and finds particular application to adaptive spatial compounding in ultrasound imaging, including an approach that enhances needle visualization without activation of a needle enhancement mode and/or a loss of image quality, improves image contrast, reduces speckle, maintains crisp and uninterrupted vessel walls and organ boundaries, and/or reduces noise.

BACKGROUND

Ultrasound imaging provides a real-time image with information about the interior of an object or a subject such as tissue, organs, etc. With one example, an excitation pulse is provided to a transducer array. At least a sub-set of the elements of the array receive the pulse and converts the electrical pulse to a pressure wave/ultrasound signal. The pressure wave is transmitted by the transducer array during a transmit operation, propagates in a medium, and interacts with the medium. Such interaction results in, among other things, echoes, which are reflections back towards the transducer.

The elements receive the echoes during a receive operation and convert the reflections to analog signals. For each receive operation, the analog signals are amplified, converted to digital signals, and beamformed to produce a scan line of radio frequency (RF) data. With delay-and-sum beamforming, the digital signals are time delayed, weighted, and then summed to produce the scan lines. The scan lines are further processed (e.g., band-pass filtering, envelope detection, logarithmic compression, etc.), scan converted, and displayed as frame/2-D image (e.g., a B-mode image).

The echoes include specular reflections from specular reflectors such as smooth surfaces of a vessel wall, muscle, an instrument such as a biopsy needle, etc., scatter from diffuse reflectors such as non-smooth surfaces and structure smaller than a wavelength of the emitted wave, and speckle, which is signal-dependent noise due to constructive and destructive coherent interferences of echoes from scatterers that manifests as a granular pattern in the B-mode image, reducing contrast and image quality. An approach to reduce or remove speckle includes spatial compounding followed by filtering with a filter configured for speckle reduction.

Spatial compounding is the process of registering and combing multiple images of the same structure that were acquired at different times and different angles of insonation/incidence to form a single compounded frame. The individual frames can be obtained by holding the transducer at a fixed position and transmitting the pressure waves at different angles via electronic beam steering and/or electronically controlled mechanical steering of the array of transducer elements inside the scanhead. To form a single compounded image, the images acquired at the different steering angles are aligned and combined. Alignment can be achieved based on transducer array geometry, steering angles, sampling frequency and/or a speed of sound in the insonated tissue.

Generally, this approach computes and utilizes a mean pixel value across the multiple images at the different angles of insonation for each pixel in the compounded image, which can smooth the image, and, hence, reduce speckle. Unfortunately, the images acquired with steered pressure waves tend to have higher levels of clutter, e.g., due to grating lobes created by echoes from angles other than the pressure wave direction, which reduces contrast in the steered scans and can obscure the view of blood vessels, cysts, etc. and break continuous contours of the vessel walls. In addition, specular reflectors such as needles can reflect the pressure wave away from the transducer array, which may result in decreasing a visibility of a needle.

Examples are depicted in FIGS. 1 and 2. In both FIG. 1 and FIG. 2, each acquisition is at a same location, but a different angle of insonation. In FIG. 1, a first image 1021 acquired at a first angle includes a vessel 104 with blur (illustrated via a lighter shade of gray) due to grating lobes, an ith image 102; acquired at an ith angle includes the vessel 104 without blur induced by the steering angle (illustrated via a darker shade of gray), and an nth image 102, acquired at an nth angle includes the vessel 104 with blur (illustrated via the lighter shade of gray) due to grating lobes. As a consequence, the mean pixel values computed and utilized for the compounded image will include blur and can visibly obscure the vessel and break continuous contours of the vessel wall.

In FIG. 2, a first pressure wave 2021 transmitted at a first angle reflects off an instrument 204 in a direction 206 other than a direction of the transmitted pressure wave, resulting in a weaker signal from the instrument (illustrated via a lighter shade of gray), an ith pressure wave 202; transmitted at an ith angle reflects off the instrument 204 in yet another direction 208 other than the direction of the transmitted pressure wave, resulting in a weaker signal from the instrument (illustrated via a medium shade of gray), and an nth pressure wave $202n$ transmitted at an nth angle reflects off the instrument 204 in a direction 210 closer to the direction of the transmitted pressure wave relative to the first and ith angles, providing a stronger signal from the instrument (illustrated via a darker shade of gray). As a consequence, the mean pixel values computed and utilized for the compounded image will include the weaker signals, which can decrease a visibility of a needle.

In view of at least the foregoing, there is an unresolved need for an improved spatial compounding approach in ultrasound imaging.

SUMMARY

Aspects of the application address the above matters, and others. This summary introduces concepts that are described in more detail in the detailed description. It should not be used to identify essential features of the claimed subject matter, nor to limit the scope of the claimed subject matter.

In one aspect, an ultrasound imaging system includes a transducer array configured to transmit a plurality of ultrasound signals, each at a different angle of insonation. The transducer array is further configured to receive, for each of the plurality of ultrasound signal, an echo signal. The transducer array is further configured to generate an electrical signal indicative of each of the echo signals. The ultrasound imaging system further includes a beamformer configured to beamform the electrical signals and produce radio frequency (RF) signal for each of the different angles of insonation. The ultrasound imaging system further includes an envelope detector configured to detect an envelope of each of the RF signals for each of the different angles of insonation. The ultrasound imaging system further includes a compressor configured to compress each of the envelopes to produce frames of data for each of the different angles of insonation. The ultrasound imaging system further includes a compounder configured to adaptively compound the frames of data for each of the different angles of insonation to generate a compounded image. The ultrasound imaging system further includes a display configured to display the compounded image.

In another aspect, a computer-implemented method includes transmitting a plurality of ultrasound signals, each at a different angle of insonation. The computer-implemented method further includes receiving, for each of the plurality of ultrasound signal, an echo signal. The computer-implemented method further includes generating an electrical signal indicative of each of the echo signals. The computer-implemented method further includes beamforming the electrical signals to produce radio frequency (RF) signal for each of the different angles of insonation. The computer-implemented method further includes detecting an envelope of each of the RF signals for each of the different angles of insonation. The computer-implemented method further includes compressing each of the envelopes to produce frames of data for each of the different angles of insonation. The computer-implemented method further includes adaptively compounding the frames of data for each of the different angles of insonation to generate a compounded image.

In another aspect, a computer readable medium is encoded with computer executable instructions, which, when executed by a processor, cause the processor to transmit a plurality of ultrasound signals, each at a different angle of insonation. The instructions further cause the processor to receive, for each of the plurality of ultrasound signal, an echo signal. The instructions further cause the processor to generate an electrical signal indicative of each of the echo signals. The instructions further cause the processor to beamform the electrical signals and produce radio frequency (RF) signal for each of the different angles of insonation. The instructions further cause the processor to detect an envelope of each of the RF signals for each of the different angles of insonation. The instructions further cause the processor to compress each of the envelopes to produce frames of data for each of the different angles of insonation. The instructions further cause the processor to adaptively compound the frames of data for each of the different angles of insonation to generate a compounded image.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings in which like references indicate similar elements.

FIG. 1 shows a prior art example in which compounding images of a same structure and acquired at different angles of insonation can introduce blur and visibly obscure vessels and break continuous contours of a vessel wall.

FIG. 2 shows a prior art example in which compounding images of a same structure and at different angles of insonation can decrease a visibility of a specular reflector such as a needle.

FIG. 3 schematically illustrates a non-limiting example of an imaging system configured for ultrasound imaging, including modes of operation and timing diagrams, in accordance with an aspect of an embodiment(s) herein.

DETAILED DESCRIPTION

Figure 4:
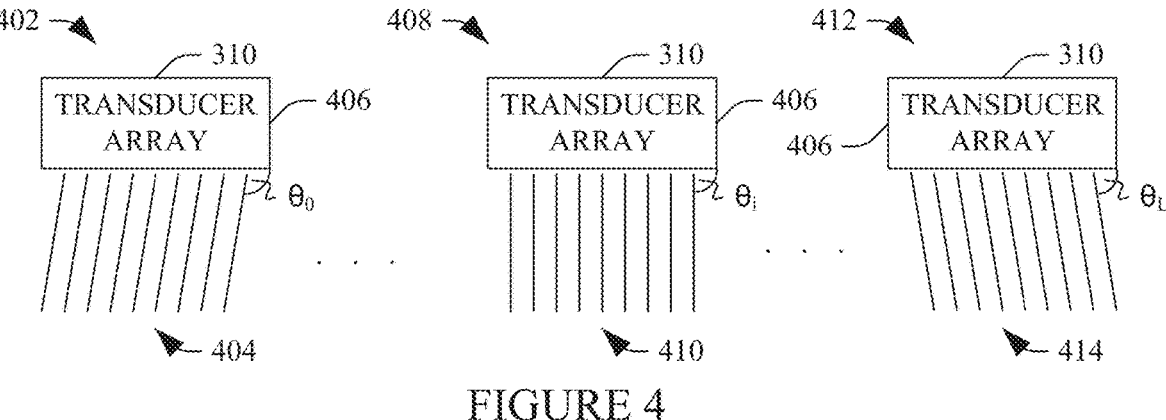
FIG. 4 schematically illustrates a non-limiting example of transmit operations for a same structure at different angles of insonation to acquire data for compounding, in accordance with an aspect of an embodiment(s) herein.

Ultrasound imaging provides a real-time image with information about the interior of an object or a subject such as tissue, organs, etc. However, ultrasound images are susceptible to speckle, which is signal-dependent noise due to constructive and destructive coherent interferences of echoes from scatterers that manifests as a granular pattern in the image, which can reduce contrast and/or image quality. Approaches for mitigating speckle, such as spatial compounding that computes and utilizes a mean pixel value across the multiple images for each pixel in the compounded image, have resulted in compounded images with higher levels of clutter, which can reduce image contrast, obscure the view of scanned structure such as vessels, cysts, etc. and break continuous contours of the structure such as vessels, and/or decrease visibility of needles.

Described herein is an adaptive spatial compounding approach that mitigates one or more of the aforementioned shortcomings and/or other shortcomings of other spatial compounding approaches. As described in greater detail below, in one instance, the adaptive spatial compounding approach determines a pixel for each pixel in the compounded image based on a signal-to-noise ratio (SNR) determined from the envelope signal and either speckle analysis of the envelope signal or image analysis of the frame data. In one instance, the adaptive spatial compounding approach described herein can enhance needle visualization without activation of a needle enhancement mode and/or a loss of image quality, improve image contrast, reduce speckle, maintain crisp and uninterrupted vessel walls and organ boundaries, and/or reduce noise.

FIG. 3 schematically illustrates a non-limiting example of an ultrasound system 302. The ultrasound system 302 includes a probe 304 and a console 306. In the illustrated embodiment, the probe 304 and the console 306 interface with each other via a communication channel 308, which includes wired (e.g., complimentary interfaces and a cable therebetween) and/or wireless technology (e.g., Wi-Fi, etc.). In another instance, the probe 304 and the console 306 are integrated in a same housing such as part of a hand-held ultrasound system, etc.

The probe 304 includes a transducer array 310. The transducer array 310 includes one or more transducer elements 312. Examples of suitable arrays include 64, 128, 192, 256, and/or other arrays, including larger and smaller arrays, one dimensional (1-D) or two dimensional (2-D), etc. The transducer array 310 can be linear, curved, and/or otherwise shaped, fully populated, sparse and/or a combination thereof, etc. The one or more transducer elements 312 are configured to convert an excitation electrical signal to an ultrasound pressure field and convert a reflected ultrasound pressure field to an electrical signal.

By way of non-limiting example, the one or more transducer elements 312 can be selectively excited via an excitation electrical (pulsed) signal, which causes at least a sub-set of the transducer elements 312 to transmit an ultrasound pressure field into an examination or scan field of view. The ultrasound pressure field may include a focused ultrasound beam, a defocused (spherical) wave, and/or other ultrasound signal. The one or more transducer elements 312 receive echo signals and generate analog electrical signals indicative thereof. The echo signals are generated in response to the transmitted ultrasound pressure field interacting with structure, such as tissue and/or blood cells flowing in a portion of a vessel.

The console 306 includes transmit circuit 314 configured to generate the excitation electrical signal provided to transducer array 310 for transmitting the ultrasound pressure field. In one instance, this includes generating delays for individual elements 312 of the transducer array 310, e.g., for transmit focusing, beam steering, etc. For ultrasound scans that include spatial compounding, the transmit circuit 314 generates an excitation electrical signal at each of the different angles of insonation.

Briefly turning to FIG. 4, examples of transmit operations for spatial compounding is schematically illustrated. In this example, the transducer array 310 transmits at L+1 different angles, where L is a positive integer greater than one, including an angle $\theta_0$, ..., $\theta_i$, ..., and an angle $\theta_L$. For a transmit interval 402, the transducer array 310 transmits a beam 404 at the angle $\theta_0$ with respect to a transducing surface 406 of the transducer array 310. For a transmit interval 408, the transducer array 310 transmits a beam 410 at an angle $\theta_i$ with respect to a transducing surface 406 of the transducer array 310. For a transmit interval 412, the transducer array 310 transmits a beam 414 at an angle $\theta_L$, with respect to the transducing surface 406 of the transducer array 310.

Although FIG. 4 shows transmit operations for three (3) different angles, it is to be understood that more or less transmit operations are contemplated herein. For example, in another instance, the transmit circuit 314 transmits for five different angles, etc. This pattern is repeated M times, wherein M is an integer greater than or equal to one. Examples suitable angles $\theta$ include ninety (90) degrees, one hundred (100) degrees, eighty (80) degrees, etc. with respect to the transmitting surface. For this case, in one instance, $\theta_0$ equals a minimum angle, $\theta_i=0$, and an angle $\theta_L$ equals a minimum angle. With respect to a perpendicular direction from the transmitting surface, the angles can be designated in terms of positive and negative degrees, e.g., positive ten (+10) degrees, and negative ten (−10) degrees.

Returning to FIG. 3, the console 306 further includes receive circuit 316 configured to receive the analog electrical signals. For ultrasound scans that include spatial compounding, the receive circuit 316 receives analog electrical signals from the elements 312 corresponding the echoes received at each of the angles of insonation. In one instance, the receive circuit 316 is further configured to pre-process the analog electrical signals, e.g., amplify, digitize, focus, and/or otherwise process the analog electrical signals.

With reference to FIG. 4, each of the transmit interval 402, 408 and 412 will have a corresponding receive operation. For example, for the transmit interval 402 at angle $\theta_0$ there will be a receive operation for the angle $\theta_0$ to receive the echoes. For the transmit interval 408 at angle $\theta_i$ there will be a receive operation for the angle $\theta_i$ to receive the echoes. For the transmit interval 412 at angle $\theta_L$ there will be a receive operation for the angle $\theta_L$ to receive the echoes. For each additional transmit interval at another angle, there will be an additional receive operation for that angle to receive the echoes.

Returning to FIG. 3, the console 306 further includes a switch 318 configured to switch between the transmit circuit 314 and the receive circuit 316, e.g., by electrically connecting the transmit circuit 314 to the transducer array 310 for a transmit operation and electrically connecting the receive circuit 316 to the transducer array 310 for a receive operation. In an alternative instance, separate switches are employed for each of the transmit circuit 314 and the receive circuit 316.

Returning to FIG. 3, the console 306 further includes a switch 318 configured to switch between the transmit circuit 314 and the receive circuit 316, e.g., by electrically connecting the transmit circuit 314 to the transducer array 310 for a transmit operation and electrically connecting the receive circuit 316 to the transducer array 310 for a receive operation. In an alternative instance, separate switches are employed for each of the transmit circuit 314 and the receive circuit 316.

The console 306 further includes a beamformer 320. For receive operations, the beamformer 320 is configured to beamform, e.g., via delay-and-sum (e.g., a matched-filter beamformer, etc.) and/or other beamforming, the signals from the receive circuit 316 and construct a scanplane of scanlines of radiofrequency (RF) data for the echoes for each receive operation.

Figure 5:
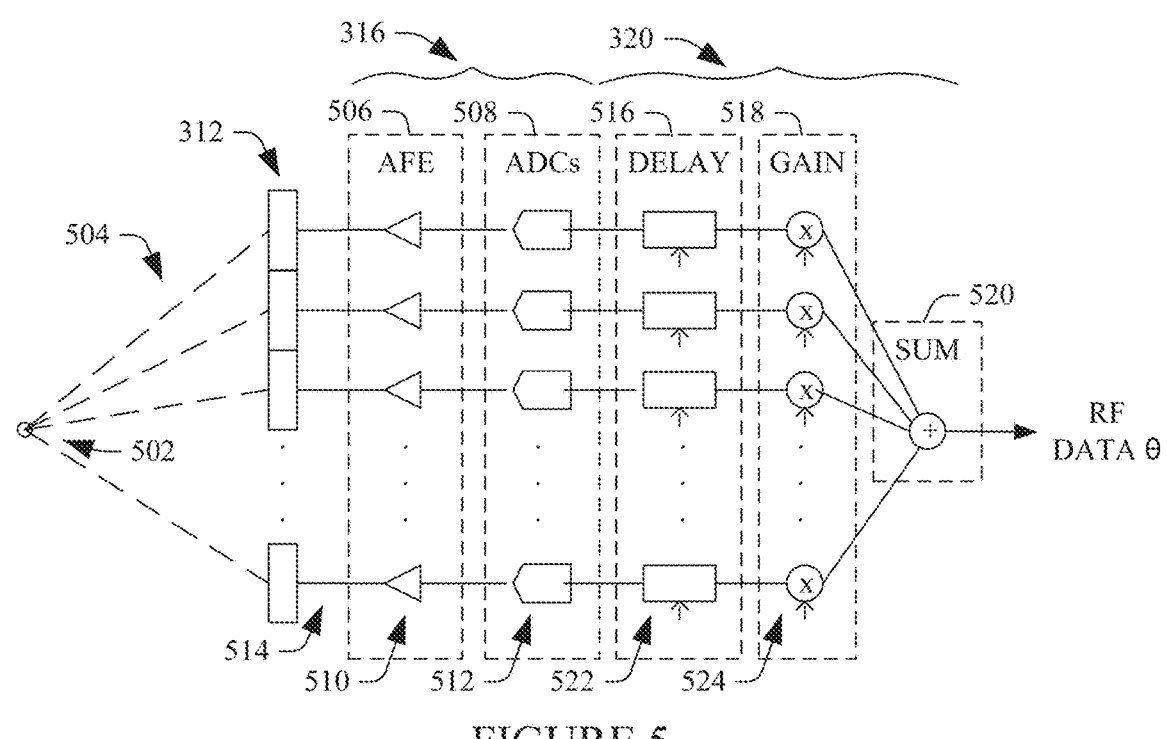
FIG. 5 schematically illustrates an example of front end and beamforming components of the imaging system of FIG. 3, in accordance with an aspect of an embodiment(s) herein.

Briefly turning to FIG. 5, an example of the receive circuit 316 and the beamformer 320 in connection with an acoustical focal point 502, echoes 504, and the elements 312 (FIG. 3) is schematically illustrated.

In this example, the receive circuit 316 includes an analog front end (AFE) 506 and an analog to digital converter (ADC) 508. The AFE 506 includes a set of amplifiers 510 and a corresponding set of ADCs 512 for each set of channels 514. Each of the amplifiers 510 amplifies a corresponding analog electrical signal from a micro-volt level to a voltage range of the ADCs 512. In one instance, a gain of the channel 308 is set to amplify weak signals as high as possible without causing clipping of the signals. Each of the ADCs 512 digitizes an amplified electrical signal.

The beamformer 320 includes delay circuit 516, gain circuit 518, and an adder/summer ("SUM") 520. The delay circuit 516 includes delay circuits 522 for each of the channels 514, and the gain circuit 518 includes gain circuits 524 for each of the channels 514. Each of the delay circuits 522 applies a corresponding delay, and each of the gain circuits 524 applies a corresponding gain/weight. The adder 520 adds/sums the delayed and weighted signals. In one instance, a matched filter matched to an expected received echo-pulse shape (bandwidth) operates on the delayed and weighted signals. The output of the beamformer 320 includes RF data for the corresponding angle of insonation $\theta$, where $\theta$ is $\theta_0, \ldots, \theta_i, \ldots,$ or $\theta_L$.

Figures 6, 7, 8:
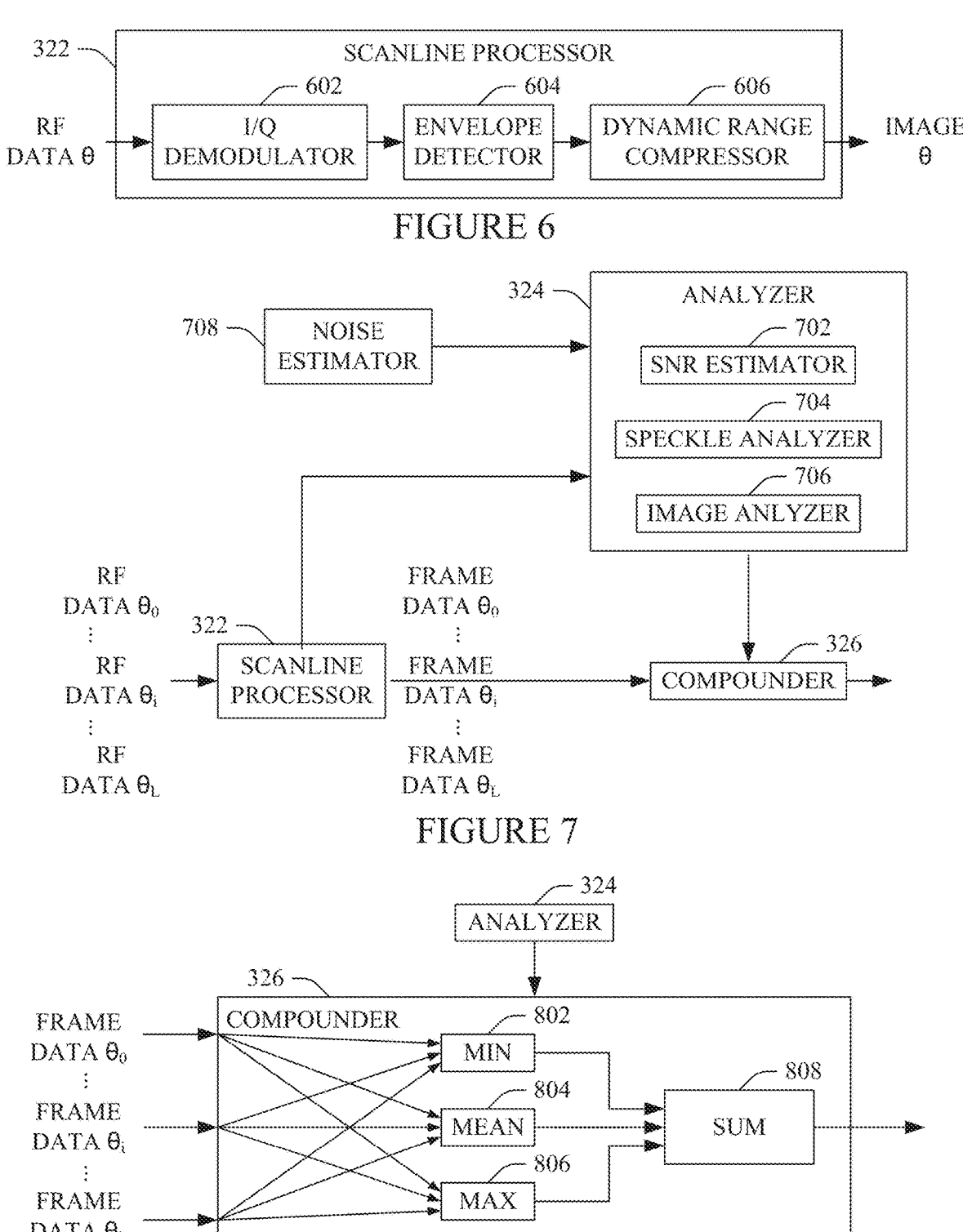
FIG. 6 schematically illustrates an example of a scanline processor of the imaging system of FIG. 3, in accordance with an aspect of an embodiment(s) herein.
FIG. 7 schematically illustrates an example of an analyzer of the imaging system of FIG. 3 that includes a single-to-noise estimator and a speckle analyzer and/or an image analyzer, in accordance with an aspect of an embodiment(s) herein.
FIG. 8 schematically illustrates an example of a compounder of the imaging system of FIG. 3 that employs the output of the analyzer to compound images, in accordance with an aspect of an embodiment(s) herein.

Returning to FIG. 3, the console 306 further includes a scanline processor 322 configured to perform other processing on the data such as filtering (e.g., via a Finite Impulse Response (FIR) filter, an Infinite Impulse Response (IIR) filter, etc.), time gain compensation (TGC), I/Q demodulation, envelope detection, logarithmic compression, noise rejection, and/or other processing, and output frames of data. FIG. 6 schematically illustrates an example of the scanline processor 322.

In FIG. 6, the example scanline processor 322 includes an in-phase and quadrature (I/Q) demodulator ("I/Q") 602, an envelope detector ("ENV") 604 and a dynamic range compressor ("DRC") 606. The scanline processor 322 receives, as input, the RF signal produced by the beamformer 320 for each angle of insonation, in parallel and/or series. The I/Q demodulator 602 is configured to down mixes the RF signal and may also apply low pass filtering and/or decimation. This may include employing a Hilbert Transform, a combination of a Complex-Demodulation Band Pass Filter and optional decimation, and/or other processing. The I/Q demodulator 602 outputs the I/Q signal. In another instance, the I/Q demodulator 602 is omitted.

The envelope detector 604 receives, as input, the I/Q signal from the I/Q demodulator 602 (or the RF signal from the beamformer 320 where the I/Q demodulator 602 is omitted), and detects, extracts and outputs an envelope (i.e., an amplitude) of the I/Q signal (or the RF signal). In one instance, this is achieved using a Hilbert transform and/or other approach. The dynamic range compressor 606 compresses the extracted envelope, reducing the dynamic range, e.g., to reduce the dynamic range to a predetermined display precision by a logarithmic (log)-based dynamic range compression and/or otherwise, and outputs a scanline. The scanline processor 322 outputs the processed scanlines as a frame/image (e.g., a B-mode image).

Returning to FIG. 3, the console 306 further includes an analyzer 324. In the illustrated example, the analyzer 324 receives, as input, data from the scanline processor 322. As described in greater detail below, the analyzer 324 is configured to analyze the data from the scanline processor 322 by at least performing noise analysis and either signal or image analysis, where the noise analysis includes determining a SNR, the signal analysis includes determining speckle statistics, and the image analysis includes determining image characteristics.

The console 306 further includes a compounder 326 configured to spatially compound (e.g., via a weighted sum) frames of data based on the output from the analyzer 324. As described in greater detail below, the compounder 326, based on a set of rules or algorithm, determines a pixel value of each pixel of the compounded image based on the output of the analyzer 324. In another words, the compounder 326 employs an adaptive spatial compounding algorithm for each pixel in the compounded image. As briefly described herein, the output from the analyzer 324 facilitates mitigating one or more of the shortcomings of existing spatial compounding approaches and/or other shortcomings of other spatial compounding approaches.

For example, the approach described herein can mitigate, during speckle removal, increasing clutter and reducing contrast in steered scans and obscuring a view of blood vessels, cysts, etc. and breaking continuous contours of vessel walls, and/or decreasing visibility of a specular surface, relative to a configuration that omits employing the approach described herein. As such, the approach described herein can reduce speckle and enhance needle visualization without a needle enhancement mode and/or a loss of image quality, improve image contrast, maintaining crisp and uninterrupted vessel walls and organ boundaries, and/or reduce noise.

The console 306 further includes a scan converter 328 and a display 330. The scan converter 328 is configured to scan convert the compounded image into a coordinate system of the display 330. The scan converter 328 can be configured to employ analog and/or digital scan converting techniques. The scan converted data can be displayed on the display 330 and/or other display monitor.

The console 306 further includes a user interface (UI) 332. The user interface 332 includes one or more input devices such as a button, a knob, a slider, a touch screen, a mouse, a keyboard, etc.) and/or other input device, and/or one or more output devices such as a visible, audible, etc. indicator. The UI 332 allows a user to control an operation of the system 302. For example, in one instance, the UI 332 receives an input indicative of an imaging protocol employing the adaptive spatial compounding described herein.

The console 306 further includes a controller 334. The controller 334 includes a processor(s) such as a microprocessor (μP), a central processing unit (CPU), a graphics processing (GPU), etc., and memory, which stores the adaptive spatial compounding algorithm described herein. The controller 334 is configured to control one or more of the transmit circuit 314, the receive circuit 316, the switch 318, the beamformer 320, the scanline processor 322, the analyzer 324, the compounder 326, the scan converter 328, the display 330, and/or the user interface 332. One or more of these components of the console 306 can be implemented in software and/or hardware.

FIG. 7 schematically illustrates an example the analyzer 324. The analyzer 324 includes a signal-to-noise ratio (SNR) estimator 702 and at least one of a speckle analyzer 704 and an image analyzer 706. Where the analyzer 324 includes both the speckle analyzer 704 and the image analyzer 706, one or both of the speckle analyzer 704 and the image analyzer 706 can be employed. As described in greater detail below in connection with FIG. 11, in another instance, the image analyzer 706 is omitted, and the analyzer 324 includes the SNR estimator 702 and the speckle analyzer 704. As described in greater detail below in connection with FIG. 14, in another instance, the speckle analyzer 704 is omitted, and the analyzer 324 includes the SNR estimator 702 and the image analyzer 704.

The analyzer 324 receives a noise reference level. In the illustrated embodiment, a noise estimator 708 estimates the noise reference level. In one instance, the noise estimator 708 estimates the noise reference level from data acquired at one or more of the different angles of insonation, $\theta_0$, . . . , $\theta_i$, . . . , and $\theta_L$. (e.g., $\theta$=0) without first transmitting a pressure wave. As such, the acquired data will not include any echo signal produced in response to a transmitted pressure wave. In other words, the acquired data will include only noise.

In one instance, the noise estimator 708 estimates the noise reference level based on the envelope data, prior to dynamic range compression. In another instance, the noise estimator 708 estimates the noise reference level based on a system model. An example of a model is described in U.S. patent application Ser. No. 17/304,864 (US 2021/0321990 A1) to Pedersen, filed on Jun. 28, 2012, and entitled "MODEL-BASED CONTROL OF A DYNAMIC RANGE OF AN ULTRASOUND IMAGE," which is incorporated herein by reference in its entirety.

The scanline processor 322 receives and processes the RF data from the beamformer 320 (FIG. 3) for the different angles of insonation, $\theta_0$, . . . , $\theta_i$, . . . , and $\theta_L$, and outputs frame data for the different angles of insonation, $\theta_0$, . . . , $\theta_i$, . . . , and $\theta_L$. The analyzer 324 receives data from the scanline processor 322. As described in greater detail below, in one instance the scanline processor 322 provides envelope data for the different angles of insonation, $\theta_0$, . . . , $\theta_i$, . . . , and $\theta_L$ to the analyzer 324, and, in another instance, the scanline processor 322 provides envelope data for the different angles of insonation, $\theta_0$, . . . , $\theta_i$, . . . , and $\theta_L$, along with the frame data for the different angles of insonation, $\theta_0$, . . . , $\theta_i$, . . . , and $\theta_L$, to the analyzer 324.

The SNR estimator 702 processes the data from the scanline processor 322 and the noise reference level to estimate a SNR. In one instance, the SNR estimator 702 estimates the SNR for every sample at location [m, n] based on EQUATION 1:

$$SNR[m,n] = \frac{\sum_i \sum_j env_0[m-i, n-j]}{\sum_i \sum_j noise[m-i, n-j]} \qquad \text{EQUATION 1}$$

where $env_0$ is the envelope data where $\theta$=0, noise is the noise reference level, and $$-\frac{I}{2} < i < \frac{I}{2},$$

-continued
and $$-\frac{J}{2} < j < \frac{J}{2}.$$

The SNR estimator 702 then, based on a predetermined set of rules or algorithm, determines and outputs a probability. Using a piecewise linear transfer function, e.g., as shown in FIG. 9, the SNR estimator 702 estimates the probability based on rules, as shown in EQUATION 2:

$$P_D = \begin{cases} 0, & SNR \geq SNR_H \\ \frac{SNR_H - SNR}{SNR_H - SNR_L}, & SNR_L < SNR < SNR_H \\ 1, & SNR \leq SNR\_L \end{cases} \qquad \text{EQUATION 2}$$

Figure 9:
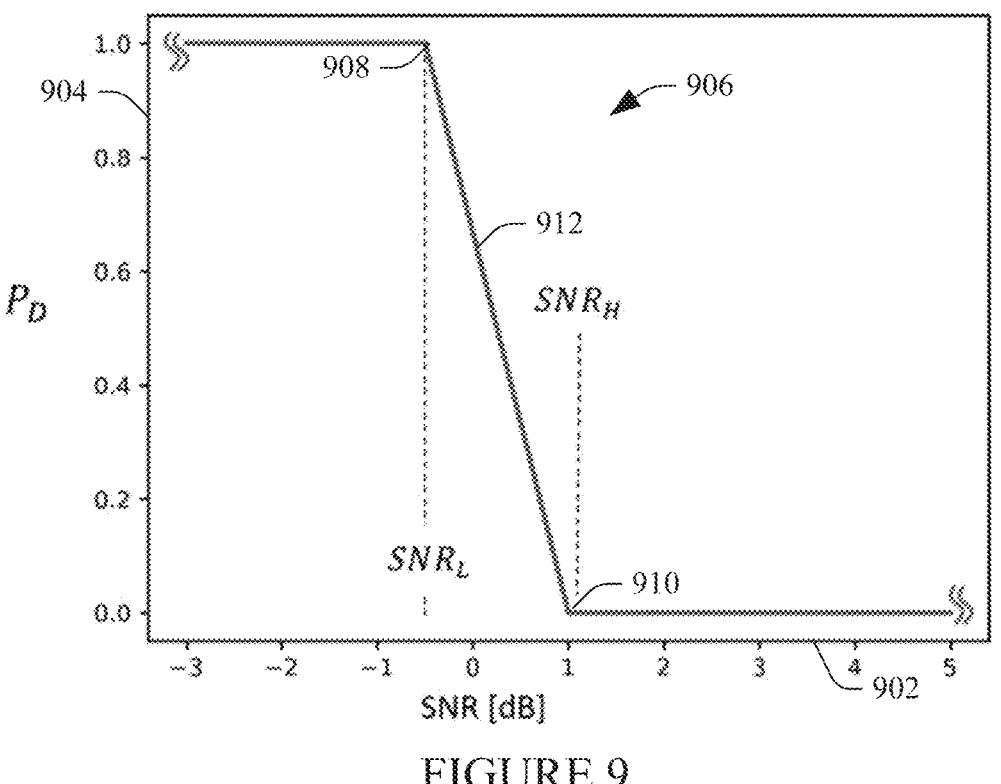
FIG. 9 illustrates an example of a linear function to determine the probability of whether a sample across the different angles of insonation represents an anechoic cyst, a vessel lumen or noise, or not, in accordance with an aspect of an embodiment(s) herein.

In FIG. 9, a first axis 902 represents SNR in units of decibels (dB) and a second axis 904 represents a probability $P_D$ with a range of values of $0 \leq P_D \leq 1$. A function 906 represents a piecewise linear transfer function. The function includes a lower SNR cutoff point ($SNR_L$) 908 representing a SNR where the $P_D$ becomes 1.0 for $SNR \leq SNR_L$. The function 906 further includes a higher SNR cutoff point ($SNR_H$) 910 representing a SNR where the $P_D$ becomes 0.0 for $SNR \geq SNR_H$. The function 906 further includes a region 912 where $P_D$ linearly decreases from 1.0 to 0.0, i.e., $0 \leq P_D \leq 1$.

Figure 10:
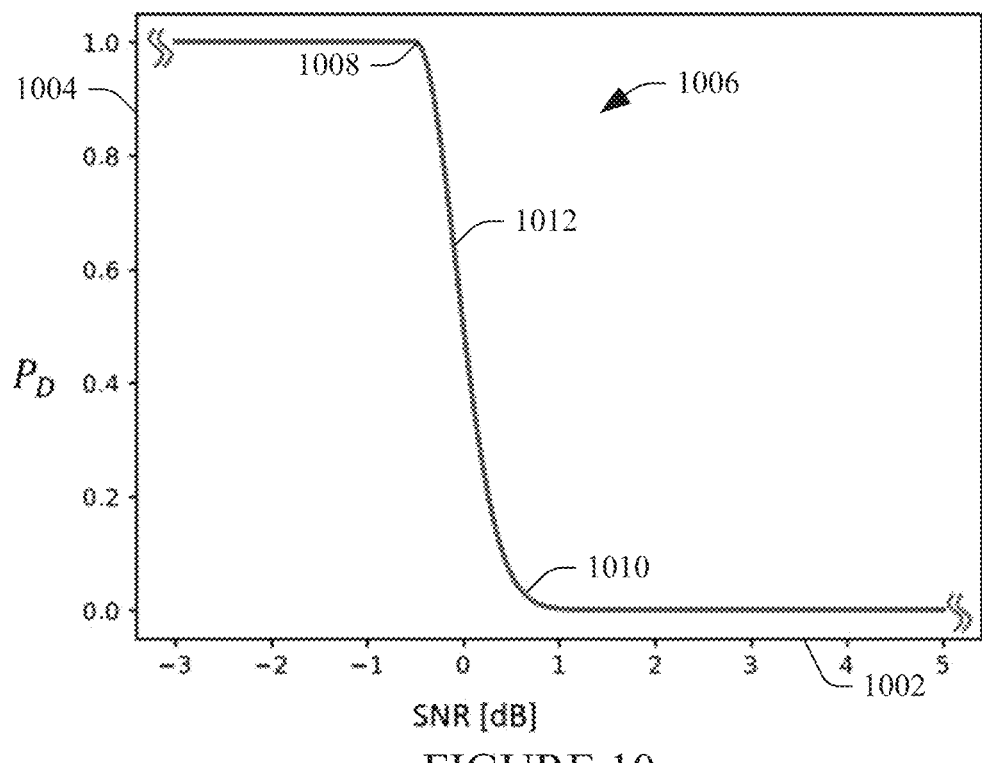
FIG. 10 illustrates an example of a non-linear function to determine whether a probability of whether a sample across the different angles of insonation represents an anechoic cyst, a vessel lumen or noise, or not, in accordance with an aspect of an embodiment(s) herein.

In another instance, the SNR estimator 702 employs a non-linear transfer function. An example of a suitable non-linear transfer function is illustrated in FIG. 10. In FIG. 10, a first axis 1002 represents a SNR in units of decibels (dB) and a second axis 1004 represents a probability $P_D$ with a range of values of $0 \leq P_D \leq 1$. A function 1006 represents a piecewise linear transfer function. The function 1006 includes a lower SNR cutoff point 1008 representing a SNR where the $P_D$ becomes 1.0, a higher SNR cutoff point 1010 representing a SNR where the $P_D$ becomes 0.0, and a region 1012 where $P_D$ non-linearly decreases from 1.0 to 0.0, i.e., $0 \leq P_D \leq 1$.

The function 906 in FIG. 9 includes abrupt cutoff points 908 and 910 and a linear transition 912 between the cutoff points 908 and 910. The function 1006 in FIG. 10 includes smoother or less abrupt cutoff points 1008 and 1010 and a non-linear transition 1012 between the cutoff points 1008 and 1010. In general, a dark region in an image can be an anechoic cyst, vessel lumen or noise, the probability $P_D$ estimates whether a pixel in the dark region is a member of a class consisting of anechoic cyst, vessel lumen or noise, or not, and, for all of the members of the class, a minimum value is utilized for the compounded images.

As described in greater detail below, the speckle analyzer 704 processes the data from the scanline processor 322 and determines and outputs a probability of a sample at location [m, n] represents speckle. As described in greater detail below, the image analyzer 706 processes the data from the scanline processor 322 and determines and outputs a probability of a sample at location [m, n] represents a reflecting surface (e.g., vessel wall, diaphragm, needle, etc., and probability of a sample at location [m, n] represents a reflecting surface (e.g., a vessel or anechoic cyst, etc.). The compounder 326, based on a predetermined set of rules, compounds the frame data for the different angles of insonation, $\theta_0$, . . . , $\theta_i$, . . . , and $\theta_L$, based on the output of the analyzer 324.

FIG. 8 schematically illustrates an example of the compounder 326 in connection with the analyzer 324. The compounder receives the frame data for the different angles of insonation, $\theta_0, \ldots, \theta_i, \ldots,$ and $\theta_L$ from the scanline processor 322 and the probabilities from the analyzer 324. The compounder 326 is configured to compound the frame data for the different angles of insonation, $\theta_0, \ldots, \theta_i, \ldots,$ and $\theta_L$ based on the probabilities. In this example, the compounder 326 includes a plurality of operator, including a minimum operator ("MIN") 802, a mean operator ("MEAN") 804, a maximum operator ("MAX") 806, and a summation operator ("SUM") 808.

The MIN operator 802 is configured to identify a minimum pixel value for each pixel of frame data across for the different angles of insonation, $\theta_0, \ldots, \theta_i, \ldots,$ and $\theta_L$. The MEAN operator 804 is configured to compute a mean pixel value for each pixel of frame data across for the different angles of insonation, $\theta_0, \ldots, \theta_i, \ldots,$ and $\theta_L$. The MAX operator 806 is configured to identify a maximum pixel value for each pixel of frame data across for the different angles of insonation, $\theta_0, \ldots, \theta_i, \ldots,$ and $\theta_L$. The SUM operator 808 is configured to sums the outputs of the operator 802, 804, and 806 based on the probabilities from the analyzer 324 to produce a compounded image.

Figure 11:
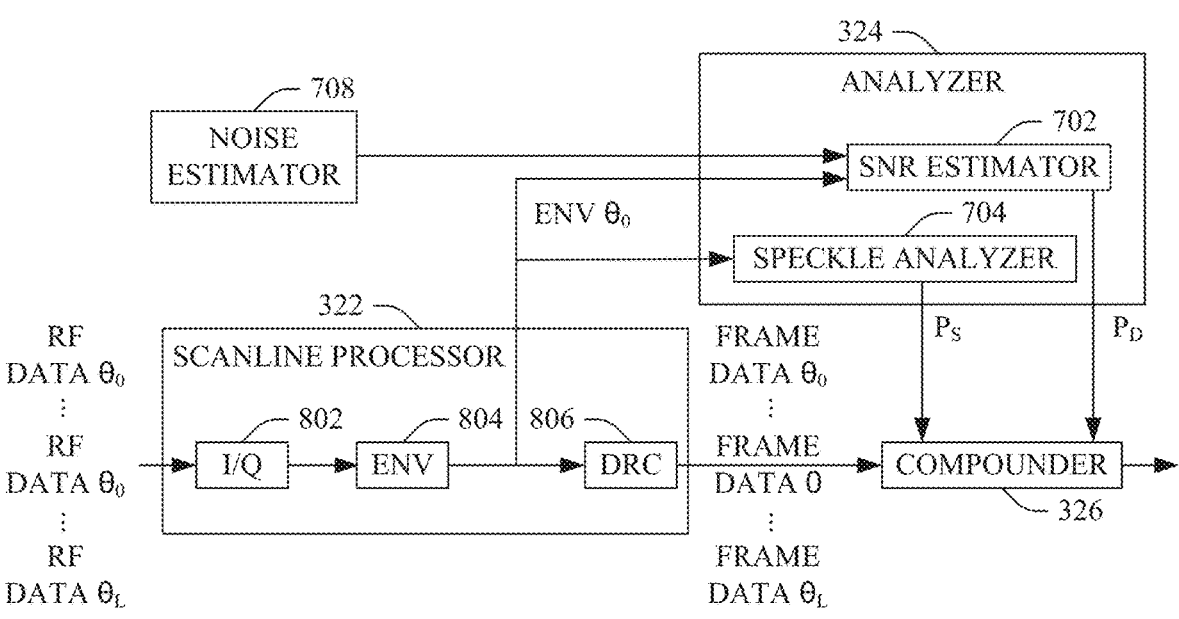
FIG. 11 schematically illustrates an example of the analyzer that includes the single-to-noise estimator and the speckle analyzer, in accordance with an aspect of an embodiment(s) herein.

FIG. 11 schematically illustrates an example of the analyzer 324 configured with the SNR estimator 702 and the speckle analyzer 704. As described in connection with FIG. 7, the SNR estimator 702 determines a probably based on data from the scanline processor 322 and the noise reference level determined by the noise estimator 708. The SNR estimator 702 provides the probably to the compounder 326. Further described in connection with FIG. 7, the speckle analyzer 704 determines a probable sample represents speckle based on the envelope data.

In this example, the speckle analyzer 704 is configured to determine speckle statistics based on EQUATION 3:

$$MSR = \frac{\mu}{\sigma} \qquad \text{EQUATION 3}$$

where $\mu$ is a mean value of the envelope data and $\sigma$ is a corresponding standard deviation. In one instance, a mean value of a sample [m, n] is computed based on EQUATION 4:

$$\mu = \frac{1}{I \cdot J} \sum_i \sum_j env[m-i, n-j] \qquad \text{EQUATION 4}$$

where env represents the envelope data $$-\frac{I}{2} < i < \frac{I}{2}$$

and $$-\frac{J}{2} < j < \frac{J}{2}.$$

In one instance, a standard deviation value of a sample [m, n] is computed based on EQUATION 5:

$$\sigma = \sqrt{\frac{1}{I \cdot J} \sum_i \sum_j (env[m-i, n-j] - \mu[m, n])}. \qquad \text{EQUATION 5}$$

In one instance, a ratio $\mu/\sigma = 1.91$ represents "perfect"/"fully developed" speckle, e.g., for abdominal, liver, brain, etc. scans.

Figure 12:
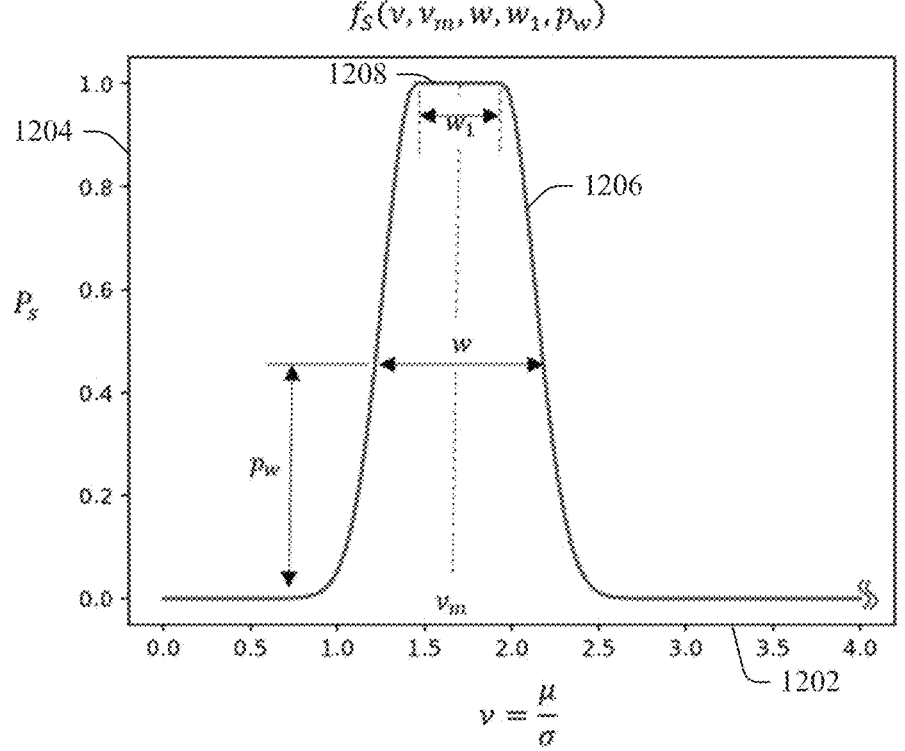
FIG. 12 illustrates an example of transfer function to determine a probability of a sample across the different angles of insonation represents speckle, in accordance with an aspect of an embodiment(s) herein.

A non-limiting example algorithm for determining the probability that a sample represents speckle based on envelope data is described in connection with FIG. 12. A first axis 1202 represents $\mu/\sigma$ and a second axis 1204 represents a probability $P_s$ with a range of values of $0 \leq P_s \leq 1$. A transfer function 1206 corresponds to: $P_s[m, n] = f_s(v[m, n], v_m, w, w_1, p_w)$, where w is a width of the function, and $0 < p_w < 1$ is a level of the function at w. In this example, the function has a generally flat top 1208 with a width $w_1$. A variable $v_m$ represents a center of the transfer function 1206.

With the transfer function 1206, the speckle analyzer 704 determines a probability $(P_s)$ based on rules or an algorithm, e.g., as shown in EQUATION 6:

$$P_s = \begin{cases} 1, & |v - v_m| < w_1/2 \qquad \text{EQUATION 6} \\ \exp\left(-\frac{\left(|v - v_m| - \frac{w_1}{2}\right)^2}{2\sigma_w^2}\right), & \text{otherwise} \end{cases}$$

where $\sigma_w$ is calculated from the widths w, $w_1$ and a level $p_w$ as shown in EQUATION 7:

$$\sigma_w = \frac{w - w_1}{2\sqrt{2 \ln(1/p_w)}}. \qquad \text{EQUATION 7}$$

When $w_1 == w$ the transfer function 1206 is a rectangular window, and when $w_1 = 0$, the transfer function 1206 is a Gaussian window. Other functions, such as a Tukey window, etc., are also contemplated herein. The speckle analyzer 704 provides the probability $(P_s)$ to the compounder 326.

Figure 13:
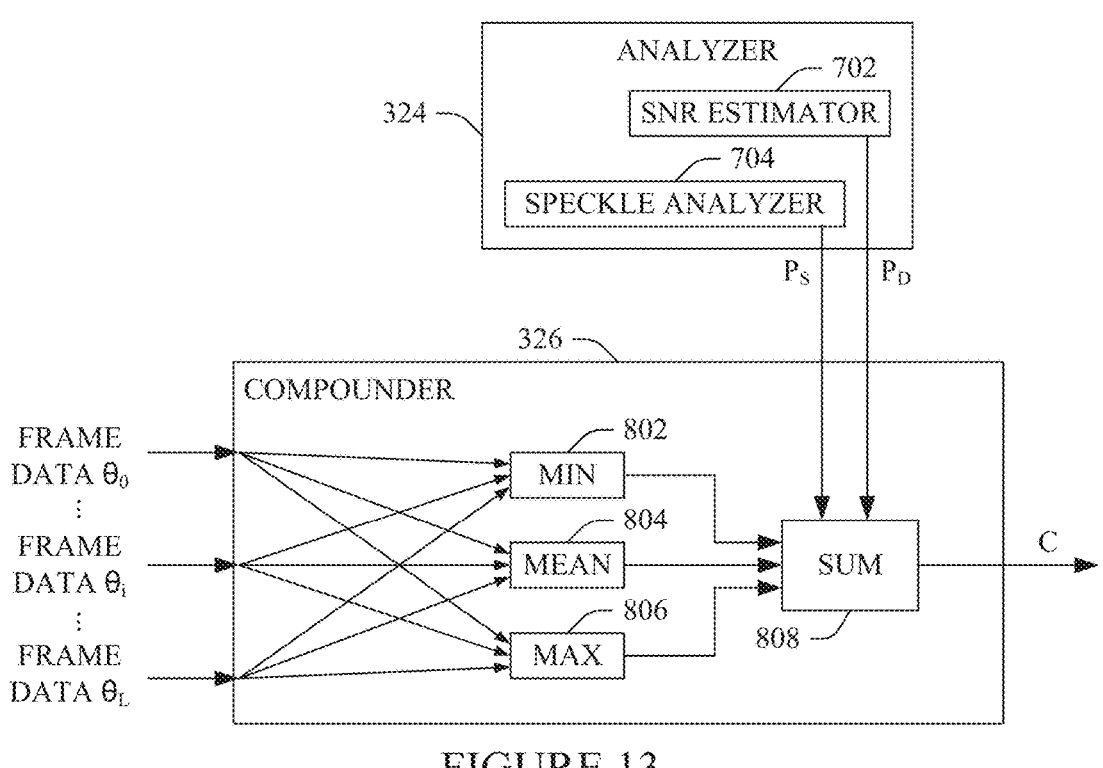
FIG. 13 illustrates an example of the compounder configured to compound images based on the probability a sample corresponds to a group (vessel, cyst and noise) and the probability the sample corresponds speckle, in accordance with an aspect of an embodiment(s) herein.

Returning to FIG. 11, the compounder 326 receives the frame data for the different angles of insonation, $\theta_0, \ldots, \theta_i, \ldots,$ and $\theta_L$ from the scanline processor 322 and the probabilities $P_s$ and $P_s$ from the analyzer 324. FIG. 13 schematically illustrates the compounder 326 configured to compound the frame data for the different angles of insonation, $\theta_0, \ldots, \theta_i, \ldots,$ and $\theta_L$ based on the probabilities $P_s$ and $P_s$. In the illustrated example, the operator 808 employs a weighted sum. An example of a suitable weighted sum is shown in EQUATION 8:

$$C = P_D \cdot \min + (1 - P_D) \cdot (P_S \cdot \text{mean} + (1 - P_S) \cdot \text{max}), \qquad \text{EQUATION 8}$$

where $0 \leq P_D \leq 1$, and $0 \leq P_s \leq 1$. The compounder 326 outputs the compounded image C.

Figure 14:
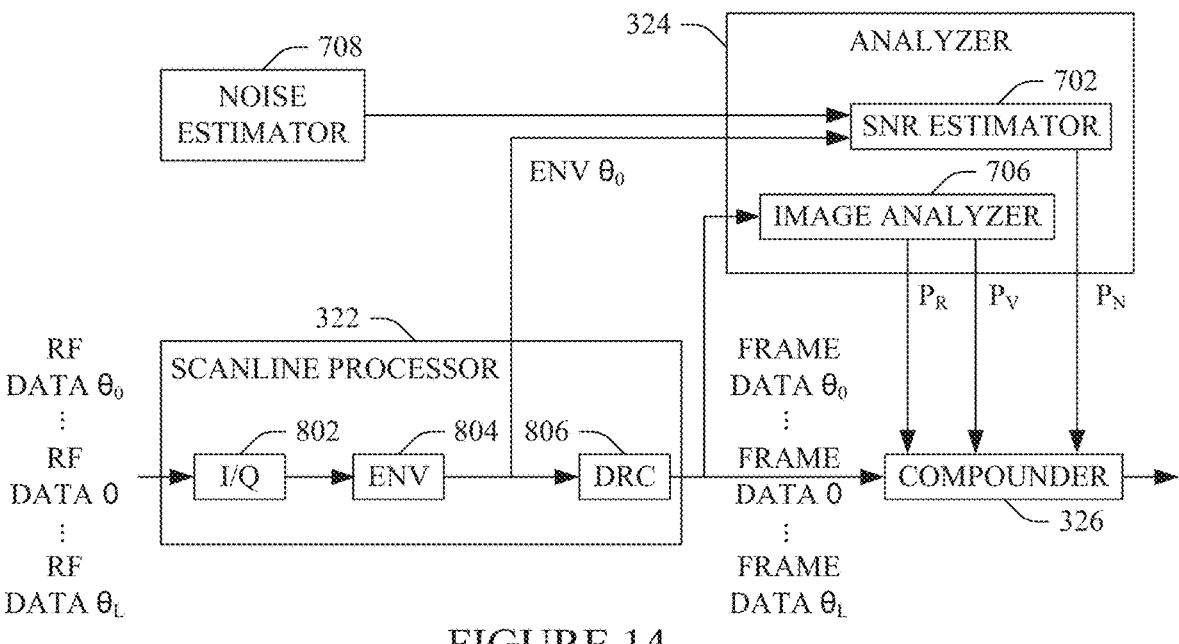
FIG. 14 schematically illustrates an example of the analyzer that includes the single-to-noise estimator and the image analyzer, in accordance with an aspect of an embodiment(s) herein.

FIG. 14 schematically illustrates an example of the analyzer 324 configured with the SNR estimator 702 and the image analyzer 706. As described in connection with FIG. 7, the SNR estimator 702 determines a probability based on data from the scanline processor 322 and the noise reference level determined by the noise estimator 708. The SNR estimator 702 provides the probability to the compounder 326. Further described in connection with FIG. 7, the image analyzer 706 determines a probability sample represents speckle based on envelope data.

Figure 15:
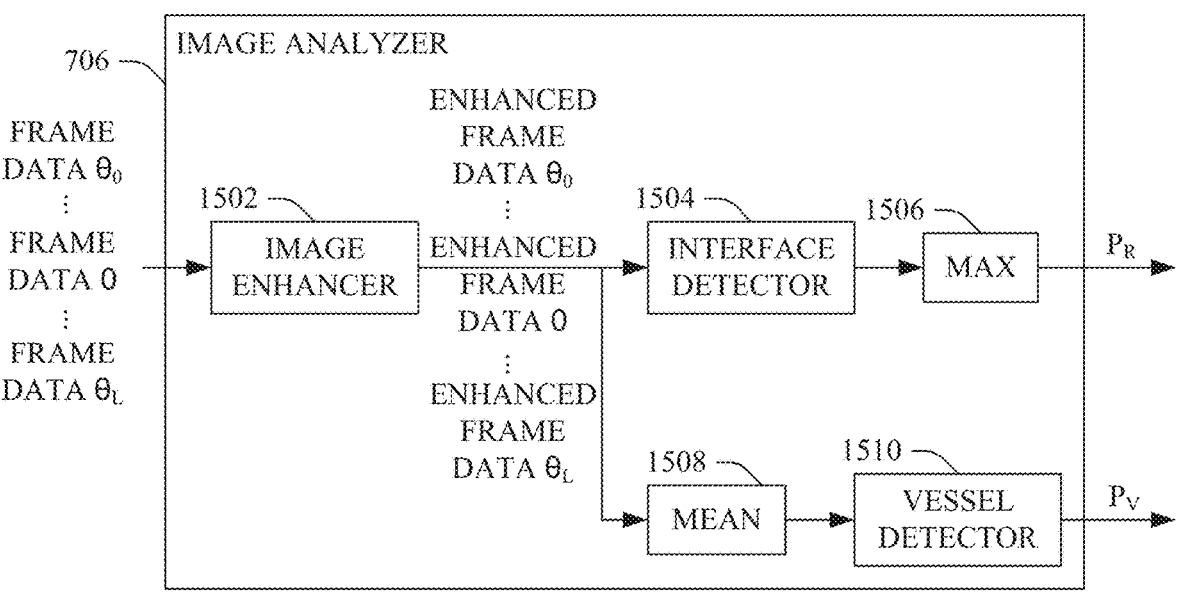
FIG. 15 schematically illustrates an example of the image analyzer that determines a probability of pixel corresponds to a reflecting surface, a probability of pixel corresponds to noise, and a probability of pixel corresponds to a group, in accordance with an aspect of an embodiment(s) herein.

FIG. 15 schematically illustrates an example of the image analyzer 706. The image analyzer 706 includes an image enhancer 1502, an interface detector 1504, a max operator ("MAX") 1506, a mean operator 1508, and a vessel detector

1510. The image analyzer 706 receives, as input, the frame data for the different angles of insonation, $\theta_0$, . . . , $\theta_i$, . . . , and $\theta_L$ from the scanline processor 322. The image enhancer 1502 processes the frame data for the different angles of insonation, $\theta_0$, . . . , $\theta_i$, . . . , and Or, to create contiguous areas with similar characteristics. In one instance, the processing at least includes unsharp masking and area opening.

The mean operator 1508 computes a mean pixel value of the pixels in the output images of the image enhancer 1502 for the different angles of insonation, $\theta_0$, . . . , $\theta_i$, . . . , and $\theta_L$ . . . . The vessel detector 1510 receives, as input, the mean image generated by the mean operator 1508 for each set of the different angles of insonation, $\theta_0$, . . . , $\theta_i$, . . . , and $\theta_L$. In one instance, the vessel detector 1510 includes a U-Net based vessel detector trained on a per-application setup, e.g., detection of carotis, detection of aorta, detection of hepatic vein, etc., and employs the trained vessel detector to identify any vessel in the mean images. The vessel detector 1510 outputs a probability $P_v$ a pixel represents a member of a group consisting of a vessel or anechoic cyst, or not.

The interface detector 1504 receives, as input, the enhanced frame data for the different angles of insonation, $\theta_0$, . . . , $\theta_i$, . . . , and $\theta_L$, from the image enhancer 1502. The interface detector 1504 processes the enhanced frame data and detects interfaces. Examples of suitable interface and vessel-like structure detection approaches include a Frangi filter. A threshold in the adaptive thresholding is estimated, e.g., from a histogram. The interface detector 1504 outputs the detected interfaces for the different angles of insonation, $\theta_0$, . . . , $\theta_i$, . . . , and $\theta_L$. The max operator 1506 determines a maximum value for each sample across the different angles of insonation, $\theta_0$, . . . , $\theta_i$, . . . , and $\theta_L$ interface detector 1504 outputs a probability $P_r$ for a reflecting surface such as a vessel wall, a diaphragm, a needle, etc. In general, needles and specular reflectors have strong echoes only in images that are steered towards the interfaces.

Figure 16:
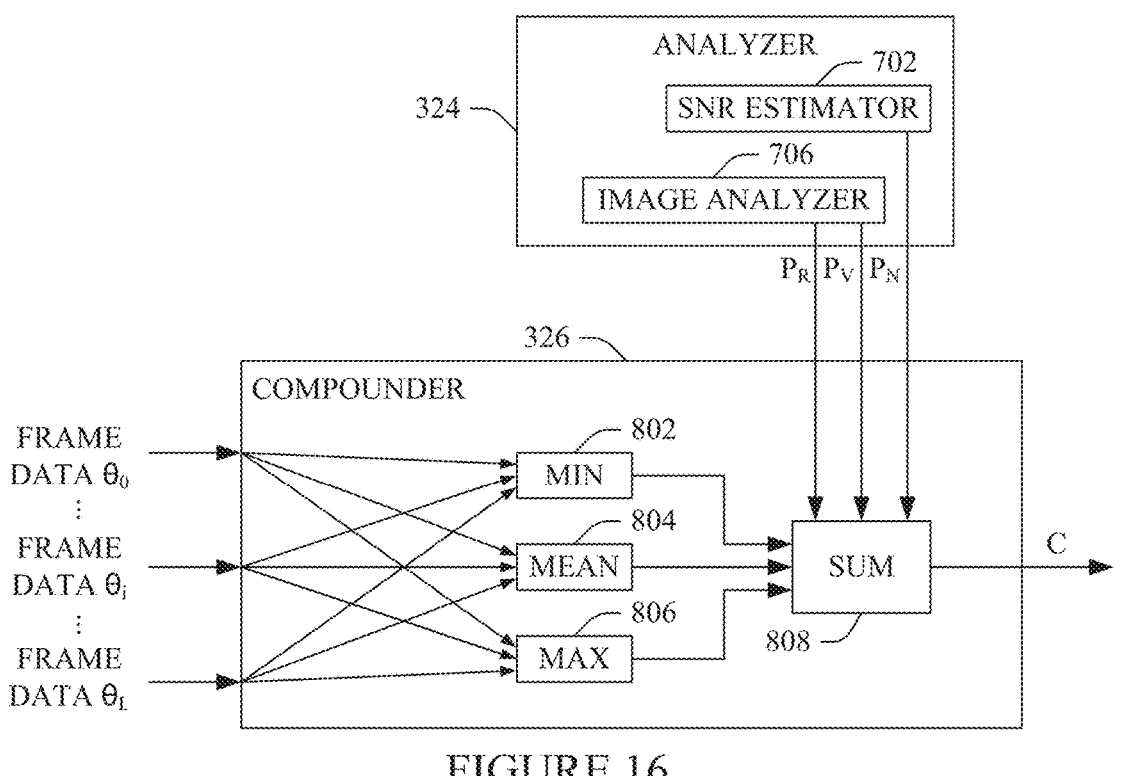
FIG. 16 illustrates an example of the compounder configured to compound images based on the probability a sample corresponds to the group and the probability the sample corresponds speckle, in accordance with an aspect of an embodiment(s) herein.

In FIG. 14, the compounder 326 receives the frame data for the different angles of insonation, $\theta_0$, . . . , $\theta_i$, . . . , and $\theta_L$ from the scanline processor 322 and the probabilities $P_R$, $P_V$ and $P_S$ from the analyzer 324. FIG. 16 schematically illustrates the compounder 326 configured to compound the frame data for the different angles of insonation, $\theta_0$, . . . , $\theta_i$, . . . , and $\theta_L$ based on the probabilities $P_R$, $P_V$ and $P_S$. In the illustrated example, the summation operator 808 employs a weighted sum. An example of a suitable weighted sum is shown in EQUATION 9:

$$C = P_R \cdot \max + (1 - P_R) \cdot (P_D \cdot \min + (1 - P_D) \cdot \text{mean}), \quad \text{EQUATION 9}$$

where $0 \leq P_D \leq 1$, $0 \leq P_R \leq 1$, $0 \leq P_V \leq 1$, $0 \leq P_N \leq 1$, and $P_D = P_V \cdot P_N$. The compounder 326 outputs the compounded image C.

Figures 17, 18:
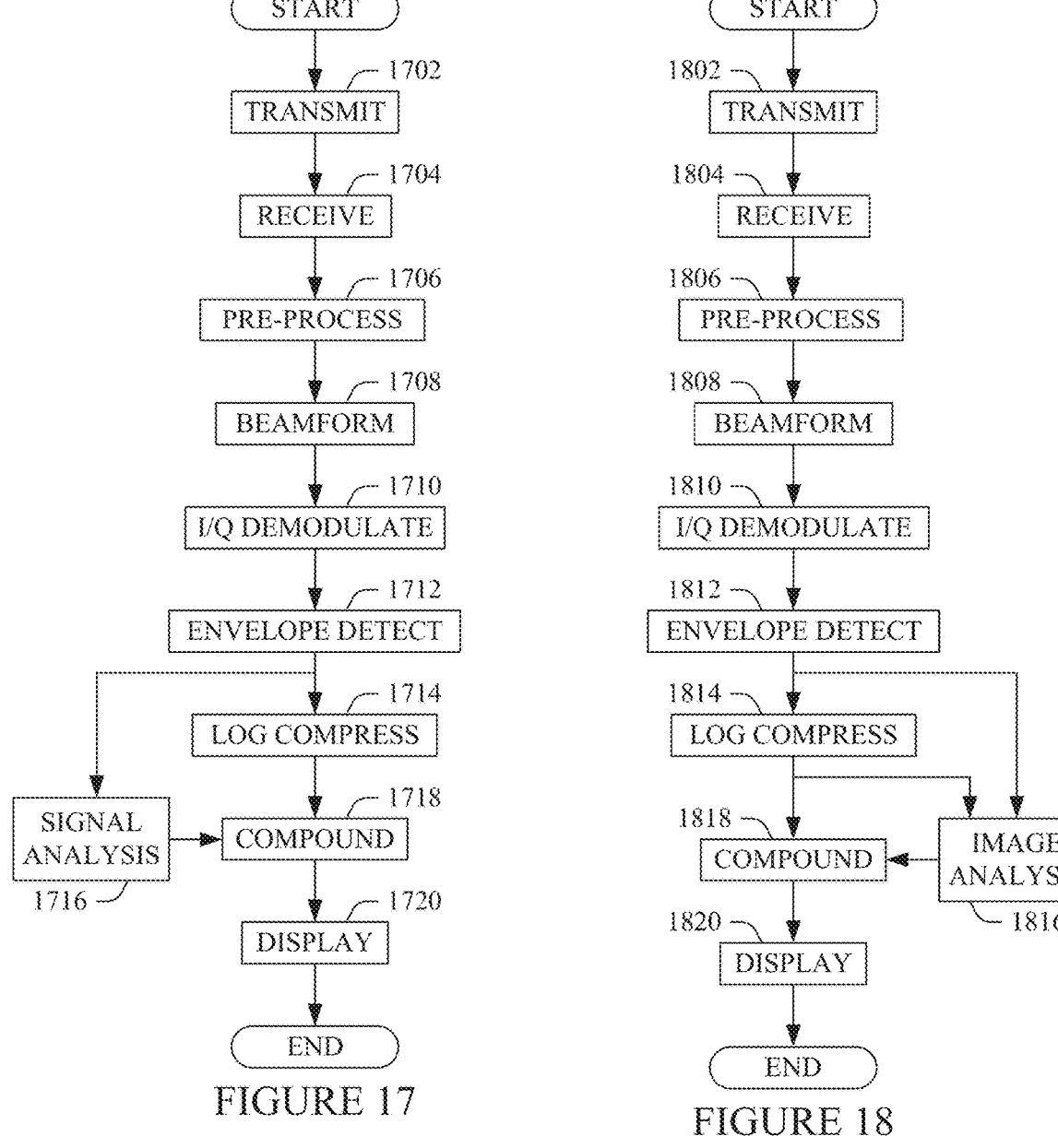
FIG. 17 illustrates a non-limiting example of a flow chart for a computer-implemented method that compounds images based at least on speckle statistics, in accordance with an embodiment(s) herein.
FIG. 18 illustrates another non-limiting example of a flow chart for a computer-implemented method based at least on image characteristics, in accordance with an embodiment(s) herein.

FIG. 17 illustrates a non-limiting example of a flow chart for a computer-implemented method based at least on speckle statistics. It is to be appreciated that the ordering of the acts in the method is not limiting. As such, other orderings are contemplated herein. In addition, one or more acts may be omitted, and/or one or more additional acts may be included.

At 1702, ultrasound pressure waves are transmitted for a set angles of insonation for an imaging procedure employing compounding, as described herein and/or otherwise. At 1704, an echoes, generated in response to interactions of the ultrasound pressure waves with structure, are received, as described herein and/or otherwise. In general, a first ultrasound pressure wave is emitted at a first angle of insonation, the receive echo generated in response thereto is received and this process is repeated for the angles in the set angles of insonation, then this repeated multiple times for the scan.

At 1706, the echoes received each receive operation are converted to analog signals, as described herein and/or otherwise. In one instance, for each receive operation, the analog signals are pre-processed, e.g., amplified, converted to digital signals. At 1708, the pre-processed signals are beamformed to produce scanlines of RF data. With delay-and-sum beamforming, the digital signals are time delayed, weighted, and then summed to produce the scanlines of RF data.

At 1710, the scanlines of RF data is I/Q demodulated, as described herein and/or otherwise. For example, in one instance the scanlines of RF data is demodulated/down mixed, producing an I/Q signal. Optionally, the demodulated data is also low pass filtered and/or decimated. This may include employing a Hilbert Transform, a combination of a Complex-Demodulation Band Pass Filter and optional decimation, and/or other processing.

At 1712, the envelope/amplitude of the I/Q signal is extracted, as described herein and/or otherwise. For example, in one instance a Hilbert transform and/or other approach is employed to extract the envelope. At 1714, the envelope is log compressed, as described herein and/or otherwise. For example, in one instance the extracted envelope undergoes log-based dynamic range compression, e.g., to reduce the dynamic range to a predetermined display precision. The resulting signal for each of the different angles of insonation is a B-mode image.

At 1716, the envelope/amplitude of the I/Q signal is analyzed, as described herein and/or otherwise. In this example, the analysis includes speckle and SNR estimation. In one instance, speckle is estimated based on the envelope/amplitude of the I/Q signal. For example, in one instance speckle is determined from data acquired at the different angles of insonation. For this, a mean and a standard deviation is determined for the samples at the different angles of insonation. A ratio of the mean to the standard deviation is then computed. A transfer function is then employed to determine a probability that a sample corresponds to speckle or not.

In one instance, the SNR is estimated based on a reference noise level and the envelope/amplitude of the I/Q signal. For example, in one instance the reference noise level is determined from data acquired at one or more of the different angles of insonation without first transmitting a pressure wave, as such data will not include any echo signal and only noise. In another instance, the reference noise level is determined based on a system model. A linear, non-linear and/or other function is employed to determine a probability a sample corresponds to a member of a group consisting of an anechoic cyst, a vessel lumen and noise, or not, based on the SNR.

At 1718, the B-mode image images for the different angles of insonation are compounded based on the probability that a sample corresponds to speckle or not and the probability the sample corresponds to the group or not, as described herein and/or otherwise. For this, minimum, mean and maximum values are determined for each sample, and a final value for each sample is computed based on a weighted combination of the probabilities and the minimum, mean and maximum values. At 1720, the compounded image is displayed.

FIG. 18 illustrates a non-limiting example of a flow chart for a computer-implemented method based at least on image characteristics. It is to be appreciated that the ordering of the acts in the method is not limiting. As such, other orderings are contemplated herein. In addition, one or more acts may be omitted, and/or one or more additional acts may be included.

At 1802, ultrasound pressure waves are transmitted for a set of angles of insonation for an imaging procedure employing compounding, as described herein and/or otherwise. At 1804, echoes, generated in response to interactions of the ultrasound pressure waves with structure, are received, as described herein and/or otherwise. In general, a first ultrasound pressure wave is emitted at a first angle of insonation, the receive echo generated in response thereto is received and this process is repeated for the angles in the set angles of insonation, then this repeated multiple times for the scan.

At 1806, the echoes received each receive operation are converted to analog signals, as described herein and/or otherwise. In one instance, for each receive operation, the analog signals are pre-processed, e.g., amplified, converted to digital signals. At 1808, the pre-processed signals are beamformed to produce scanlines of RF data. With delay-and-sum beamforming, the digital signals are time delayed, weighted, and then summed to produce the scanlines of RF data.

At 1810, the scanlines of RF data is I/Q demodulated, as described herein and/or otherwise. For example, in one instance the scanlines of RF data is demodulated/down mixed, producing an I/Q signal. Optionally, the demodulated data is also low pass filtered and/or decimated. This may include employing a Hilbert Transform, a combination of a Complex-Demodulation Band Pass Filter and optional decimation, and/or other processing.

At 1812, the envelope/amplitude of the I/Q signal is extracted, as described herein and/or otherwise. For example, in one instance a Hilbert transform and/or other approach is employed to extract the envelope. At 1814, the envelope is log compressed, as described herein and/or otherwise. For example, in one instance the extracted envelope undergoes log-based dynamic range compression, e.g., to reduce the dynamic range to a predetermined display precision. The resulting signal for each of the different angles of insonation is a B-mode image.

At 1816, the envelope/amplitude of the I/Q signal and the B-mode images are analyzed, as described herein and/or otherwise. In one instance, the SNR is estimated based on a reference noise level and the envelope/amplitude of the I/Q signal. For example, in one instance the reference noise level is determined from data acquired at one or more of the different angles of insonation without first transmitting a pressure wave as such data will not include any echo signal and only noise. In another instance, the reference noise level is determined based on a system model. A linear, non-linear and/or other function is employed to determine a probability a sample corresponds to a member of a group consisting of an anechoic cyst, a vessel lumen and noise, or not, based on the SNR.

In this example, the analysis includes image analysis and SNR estimation. For image analysis, the frame data for the different angles of insonation are processed to enhance images to create contiguous areas with similar characteristics. In one instance, the processing at least includes unsharp masking and area opening. A mean image of the enhanced images for the different angles of insonation is generated. The mean image is then processed to determine a probability that a pixel represents a member of a group consisting of vessel and anechoic cyst, or not. In addition, each of the enhanced images is processed to detect interfaces and then a maximum of a pixel value across the different angles of insonation is determined. In general, needles and specular reflectors have strong echoes only in images that are steered towards the interfaces.

At 1818, the B-mode image images for the different angles of insonation are compounded based on the probability that a sample corresponds to a reflecting surface, the probability that a sample corresponds to noise, the probability that a sample corresponds to a vessel or anechoic cyst, as described herein and/or otherwise. For this, minimum, mean and maximum values are determined for each pixel, and a final value for each pixel is computed based on a weighted combination of the probabilities and the minimum, mean and maximum values. At 1820, the compounded image is displayed.

The above can be implemented by way of computer readable instructions, encoded, or embedded on the computer readable storage medium, which, when executed by a computer processor, cause the processor to carry out the described acts or functions. Additionally, or alternatively, at least one of the computer readable instructions is carried out by a signal, carrier wave or other transitory medium, which is not computer readable storage medium.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include such additional elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only and are thus not intended to limit in any way the definition and/or meaning of the term "computer". The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present disclosure. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. An ultrasound imaging system, comprising:
a transducer array configured to:
transmit a plurality of ultrasound signals, each at a different angle of insonation;
receive, for each of the plurality of ultrasound signal, an echo signal; and
generate an electrical signal indicative of each of the echo signals;
a beamformer configured to beamform the electrical signals and produce a radio frequency (RF) signal for each of the different angles of insonation;
an envelope detector configured to detect an envelope of each of the RF signals for each of the different angles of insonation;
a signal-to-noise ratio (SNR) estimator configured to estimate an SNR based on the envelopes and a reference noise level and determine first probabilities based on the SNR that samples of the envelopes correspond to one of noise, an anechoic cyst, and a blood vessel;
a compressor configured to compress each of the envelopes to produce frames of data for each of the different angles of insonation;
a compounder configured to adaptively compound the frames of data for each of the different angles of insonation based on the first probabilities to generate a compounded image; and
a display configured to display the compounded image.

2. The ultrasound imaging system of claim 1, wherein the reference noise level includes data acquired with the transducer array without first transmitting a pressure wave.

3. The ultrasound imaging system of claim 1, further comprising:
a speckle analyzer configured to analyze the envelopes for speckle statistics, wherein the compounder is configured to adaptively compound frames based on the speckle statistics and the first probabilities.

4. The ultrasound imaging system of claim 3, wherein the compounder is configured to compute a weighted sum of the frames based on the speckle statistics and the first probabilities to generate the compounded image.

5. The ultrasound imaging system of claim 4, wherein the speckle statistics include probabilities of whether samples correspond to speckle.

6. The ultrasound imaging system of claim 5, wherein the compounder is further configured to identify minimum pixel values in the frames, compute mean pixel values of the frames and identify maximum pixel values in the frames, and compute the weighted sum of the frames based on the minimum pixel values, the mean pixel values, the maximum pixel values, the speckle probabilities and the first probabilities to generate the compounded image.

7. The ultrasound imaging system of claim 1, further comprising:
an image analyzer configured to analyze the frames for image characteristics, wherein the image compounder is configured to adaptively compound frames based on the image characteristics and the first probabilities.

8. The ultrasound imaging system of claim 7, wherein the image compounder is configured to compute a weighted sum of the frames based on the image characteristics and the first probabilities to generate the compounded image.

9. The ultrasound imaging system of claim 8, wherein the image characteristics include image probabilities of whether pixels correspond to one of a reflecting surface, a vessel and an anechoic cyst.

10. The ultrasound imaging system of claim 9, wherein the compounder is configured to identify minimum pixel values in the frames, compute mean pixel values of the frames and identify maximum pixel values in the frames, and compute a weighted sum of the frames based on the minimum pixel values, the mean pixel values, the maximum pixel values, the image probabilities and the first probabilities to generate the compounded image.

11. A computer-implemented method, comprising:

transmitting a plurality of ultrasound signals, each at a different angle of insonation;

receiving, for each of the plurality of ultrasound signal, an echo signal;

generating an electrical signal indicative of each of the echo signals;

beamforming the electrical signals to produce radio frequency (RF) signal for each of the different angles of insonation;

detecting an envelope of each of the RF signals for each of the different angles of insonation;

compressing each of the envelopes to produce frames of data for each of the different angles of insonation;

determining first probabilities based on an estimated SNR; and adaptively compounding the frames of data for each of the different angles of insonation based on the first probabilities to generate a compounded image.

12. The computer-implemented method of claim 11, further comprising:

estimating the SNR based on the envelopes and a reference noise level.

13. The computer-implemented method of claim 11, further comprising:

determining speckle statistics based on the envelopes; and adaptively compounding the frames based on the speckle statistics and the first probabilities.

14. The computer-implemented method of claim 11, further comprising:

determining image characteristics based on the frames; and adaptively compounding the frames based on the image characteristics and the first probabilities.

15. The computer-implemented method of claim 11, wherein the adaptive compounding includes computing a weighted sum of minimum pixel values, mean pixel values and maximum pixel values, and at least one of speckle statistics and image characteristics.

16. A computer readable medium encoded with computer executable instructions, which, when executed by a processor, cause the processor to:

transmit a plurality of ultrasound signals, each at a different angle of insonation;

receive, for each of the plurality of ultrasound signal, an echo signal;

generate an electrical signal indicative of each of the echo signals;

beamform the electrical signals and produce radio frequency (RF) signal for each of the different angles of insonation;

detect an envelope of each of the RF signals for each of the different angles of insonation;

compress each of the envelopes to produce frames of data for each of the different angles of insonation;

determine first probabilities based on an estimated SNR; and adaptively compound the frames of data for each of the different angles of insonation based on the first probabilities to generate a compounded image.

17. The computer readable medium of claim 16, wherein the instructions further cause the processor to:

estimate the SNR based on the envelopes and a reference noise level.

18. The computer readable medium of claim 16, wherein the instructions further cause the processor to:

determine speckle statistics based on the envelopes; and adaptively compound the frames based on the speckle statistics and the first probabilities.

19. The computer readable medium of claim 16, wherein the instructions further cause the processor to:

determine image characteristics based on the frames; and adaptively compound the frames based on the image characteristics and the first probabilities.

20. The computer readable medium of claim 16, wherein the instructions further cause the processor to:

compound the frames using a weighted sum of minimum pixel values, mean pixel values and maximum pixel values, and at least one of speckle statistics and image characteristics.

* * * * *